(12) United States Patent
Kurasaki et al.

(10) Patent No.: US 10,559,480 B2
(45) Date of Patent: Feb. 11, 2020

(54) SUBSTRATE TREATMENT APPARATUS AND SUBSTRATE TREATMENT METHOD

(71) Applicant: SCREEN Holdings Co., Ltd., Kyoto (JP)

(72) Inventors: Koji Kurasaki, Kyoto (JP); Kenji Edamitsu, Kyoto (JP); Masaharu Sato, Kyoto (JP); Kei Takechi, Kyoto (JP); Takeshi Matsumura, Kyoto (JP)

(73) Assignee: SCREEN Holdings Co., Ltd., Kyoto (JP)

( * ) Notice: Subject to any disclaimer, the term of this patent is extended or adjusted under 35 U.S.C. 154(b) by 0 days.

(21) Appl. No.: 15/890,434

(22) Filed: Feb. 7, 2018

(65) Prior Publication Data

US 2018/0247839 A1  Aug. 30, 2018

(30) Foreign Application Priority Data

Feb. 28, 2017  (JP) ................................ 2017-036442

(51) Int. Cl.
  *H01L 21/67*  (2006.01)
  *H01L 21/02*  (2006.01)
  (Continued)

(52) U.S. Cl.
  CPC ........ *H01L 21/67057* (2013.01); *B08B 3/048* (2013.01); *B08B 3/08* (2013.01);
  (Continued)

(58) Field of Classification Search
  None
  See application file for complete search history.

(56) References Cited

U.S. PATENT DOCUMENTS

2006/0042756 A1* 3/2006 Miyazaki ................ B08B 3/00
                                                    156/345.18
2008/0066863 A1   3/2008 Kiyose et al.
(Continued)

FOREIGN PATENT DOCUMENTS

| JP | H07-169822 A | 7/1995 |
|---|---|---|
| JP | 2006-100493 A | 4/2006 |
| JP | 2006-237228 A | 9/2006 |
| KR | 10-2008-0026489 A | 3/2008 |
| TW | 1538081 B | 6/2016 |

OTHER PUBLICATIONS

Office Action and Search Report dated Dec. 25, 2018 issued in counterpart Taiwanese Application No. 107101868 and English partial translation of the Office Action based on the Japanese translation attached.
(Continued)

*Primary Examiner* — Sylvia Macarthur
(74) *Attorney, Agent, or Firm* — Ostrolenk Faber LLP

(57) ABSTRACT

A substrate treatment apparatus according to the present invention is provided with a first tank that stores treatment liquid for treating a substrate and a first path that returns the treatment liquid, which has spilled over from an upper part of the first tank, to a lower part of the first tank. A second path that branches from the first path, a measurement tank that stores the treatment liquid, which has flowed in from the second path, and a pressure measurement part that measures the pressure of the treatment liquid at a predetermined depth in the measurement tank in a state in which the treatment liquid spills over from an upper part of the measurement tank are provided. Therefore, techniques for highly precisely measuring the pressure of the treatment liquid used in treatment of substrates can be provided.

11 Claims, 3 Drawing Sheets

(51) Int. Cl.
    *C03C 15/00*     (2006.01)
    *B08B 3/04*     (2006.01)
    *B08B 3/10*     (2006.01)
    *B08B 3/08*     (2006.01)
    *G01N 9/00*     (2006.01)
    *G01L 11/00*     (2006.01)

(52) U.S. Cl.
    CPC ............... *B08B 3/10* (2013.01); *G01L 11/00* (2013.01); *G01N 9/00* (2013.01); *H01L 21/02052* (2013.01); *H01L 21/67253* (2013.01); *B08B 2203/007* (2013.01); *C03C 15/00* (2013.01)

(56) References Cited

U.S. PATENT DOCUMENTS

2013/0255882 A1    10/2013    Takahashi et al. ...... 156/345.15
2018/0247839 A1*    8/2018    Kurasaki ............. C03C 23/0075

OTHER PUBLICATIONS

Notification of Reason for Refusal dated Mar. 5, 2019 in counterpart Korean Patent Application No. 10-2018-0011465 with English translation obtained from Global Dossier.
Notice of Final Rejection dated Sep. 20, 2019 in counterpart Korean Patent Application No. 10-2018-0011465 with English translation obtained from Global Dossier.

* cited by examiner

SUBSTRATE TREATMENT APPARATUS AND SUBSTRATE TREATMENT METHOD

BACKGROUND OF THE INVENTION

Field of the Invention

The present invention relates to a substrate treatment apparatus which treats substrates such as semiconductor substrates, liquid-crystal-display glass substrates, or photomask glass substrates with treatment liquid and a substrate treatment method.

Description of the Background Art

Conventionally, there is known a substrate treatment apparatus of an immersion type which treats substrates by immersing the substrates in treatment liquid such as pure water or chemical solution in a manufacturing process of substrates such as semiconductor substrates, liquid-crystal-display glass substrates, or photomask glass substrates.

The substrate treatment apparatus of the immersion type is provided with a treatment tank for storing the treatment liquid used in treatment of the substrates. Cleaning treatment, etc. of the substrates are carried out in the treatment tank.

In the treatment tank, in order to carry out uniform treatment for the substrates, the concentration of the treatment liquid in the treatment tank is controlled. As a method of measuring the concentration of the treatment liquid in the treatment tank in that process, there is a method which measures the specific weight of the treatment liquid by focusing on the fact that there is a correlation between the concentration of the treatment liquid and the specific weight of the treatment liquid (for example, see Japanese Patent Application Laid-Open No. 2006-237228).

When the specific weight of the treatment liquid is to be measured, the pressure of the treatment liquid at a predetermined depth is measured by focusing on the fact that there is a correlation between the specific weight of the treatment liquid and the pressure of the treatment liquid at the predetermined depth. In this process, if the liquid surface of the treatment liquid which is to be subjected to the measurement of the pressure is unstable, it is difficult to measure the pressure of the treatment liquid with high precision.

The position of the liquid surface in the treatment tank in which the substrates are treated varies depending on inflow and outflow of the treatment liquid used in treatment of the substrates. Therefore, it has been difficult to measure the pressure of the treatment liquid with high precision.

Moreover, if air bubbles are supplied in the treatment tank in order to remove the particles in the treatment liquid stored in the treatment tank, the variations in the liquid surface become large, and it has been more difficult to measure the pressure of the treatment liquid with high precision.

SUMMARY OF THE INVENTION

The present invention is directed to a substrate treatment apparatus which treats substrates with treatment liquid.

In one aspect of the present invention, a substrate treatment apparatus has: a first tank that stores treatment liquid for treating a substrate; a first path that returns the treatment liquid spilled over from an upper part of the first tank to a lower part of the first tank; a second path that branches from the first path; a measurement tank that stores the treatment liquid flowed in from the second path; and a pressure measurement part that measures a pressure of the treatment liquid at a predetermined depth in the measurement tank in a state in which the treatment liquid spills over from an upper part of the measurement tank.

In the measurement tank, variations in the liquid surface of the treatment liquid can be suppressed by causing the treatment liquid which flows in from the second path to overflow from the upper part. Therefore, the pressure of the treatment liquid which is in the stable state of liquid surface in the measurement tank is measured by the pressure measurement part, and, as a result, the pressure of the treatment liquid can be measured with high precision.

Preferably, a flow rate of the treatment liquid in the second path is smaller than a flow rate of the treatment liquid that returns to the first tank through the first path.

By carrying out the pressure measurement by using the treatment liquid in the second path having the smaller flow rate than that of the treatment liquid which returns to the first tank through the first path, the precision of the pressure measurement of the treatment liquid by the pressure measurement part can be increased. More specifically, in the measurement tank, variations in the liquid surface of the treatment liquid are suppressed by overflowing the treatment liquid, which flows in from the second path, from the upper part, in which, if the flow rate of the treatment liquid which flows in from the second path is low, the flow rate of the treatment liquid which overflows from the upper part of the measurement tank is also lowered, and therefore, the variations in the liquid surface are reduced. Therefore, the precision of the pressure measurement of the treatment liquid by the pressure measurement part can be increased.

Preferably, the measurement tank is provided with a first region into which the treatment liquid flows from the second path and a second region into which the treatment liquid spilled over from an upper part of the first region flows, and the pressure measurement part measures the pressure of the treatment liquid in the second region in a state in which the treatment liquid spills over from an upper part of the second region.

In the second region that is different from the first region, into which the treatment liquid flows from the second path, and stores the treatment liquid overflowed from the first region, the pressure measurement of the treatment liquid by the pressure measurement part is carried out. Herein, since there is no variation caused by the flow of the treatment liquid, which flows in from the second path, reflected by the bottom part of the measurement tank, the liquid surface of the treatment liquid in the second region has smaller variations compared with the liquid surface of the treatment liquid in the first region. Therefore, the pressure of the treatment liquid can be measured by the pressure measurement part with high precision.

Preferably, the substrate treatment apparatus further has a second tank into which the treatment liquid spilled over from the upper part of the first tank flows, in which the first path returns the treatment liquid flowed into the second tank to the lower part of the first tank, the measurement tank is disposed in the second tank, and the treatment liquid spilled over from the upper part of the measurement tank flows into the second tank.

Since the measurement tank is disposed in the second tank, the treatment liquid spilled over from the upper part of the measurement tank flows into the second tank and further flows into the first path. Therefore, the treatment liquid caused to flow into the second path for pressure measurement can be returned to the first path again, and the treatment liquid can be effectively utilized for treating the substrates.

Moreover, since the measurement tank is disposed in the second tank, piping or the like for returning the treatment liquid, which has flowed into the second path, to the first path is not required to be separately prepared.

Preferably, the substrate treatment apparatus further has an air-bubble supply part that supplies an air bubble into the first tank.

The particles in the first tank can be removed.

Preferably, the substrate treatment apparatus has a first heating part that is disposed at the first path and heats the treatment liquid returning from the first path to the first tank.

The temperature of the treatment liquid that returns from the first path to the first tank can be caused to be close to the temperature of the treatment liquid in the first tank. Therefore, temperature changes of the treatment liquid in the measurement tank can be suppressed.

Preferably, the substrate treatment apparatus has a second heating part that is disposed at the second path and heats the treatment liquid in the second path.

The temperature of the treatment liquid that flows into the measurement tank can be caused to be close to the temperature of the treatment liquid in the first tank.

Preferably, at least one hole is formed at a bottom part of the measurement tank.

When the measurement tank is to be taken out from the second tank, the treatment liquid can be prevented from remaining in the measurement tank.

The present invention is also directed to a substrate treatment method of treating substrates with treatment liquid.

In one aspect of the present invention, a substrate treatment method includes the steps of: storing treatment liquid for treating a substrate in a first tank; returning the treatment liquid spilled over from an upper part of the first tank to a lower part of the first tank through a first path; storing, in a measurement tank, the treatment liquid flowed in from a second path that branches from the first path; and measuring a pressure of the treatment liquid at a predetermined depth in the measurement tank in a state in which the treatment liquid spills over from an upper part of the measurement tank.

In the measurement tank, variations in the liquid surface of the treatment liquid can be suppressed by causing the treatment liquid which flows in from the second path to overflow from the upper part. Therefore, the pressure of the treatment liquid which is in the stable state of liquid surface in the measurement tank is measured by the pressure measurement part, and, as a result, the pressure of the treatment liquid can be measured with high precision.

Preferably, a flow rate of the treatment liquid in the second path is smaller than a flow rate of the treatment liquid that returns to the first tank through the first path.

By carrying out the pressure measurement by using the treatment liquid in the second path having the smaller flow rate than that of the treatment liquid which returns to the first tank through the first path, the precision of the pressure measurement of the treatment liquid by the pressure measurement part can be increased. More specifically, in the measurement tank, variations in the liquid surface of the treatment liquid are suppressed by overflowing the treatment liquid, which flows in from the second path, from the upper part, in which, if the flow rate of the treatment liquid which flows in from the second path is low, the flow rate of the treatment liquid which overflows from the upper part of the measurement tank is also lowered, and therefore, the variations in the liquid surface are reduced. Therefore, the precision of the pressure measurement of the treatment liquid by the pressure measurement part can be increased.

Preferably, the measurement tank is provided with a first region into which the treatment liquid flows from the second path and a second region into which the treatment liquid spilled over from an upper part of the first region flows, and the pressure of the treatment liquid is measured in the second region in a state in which the treatment liquid spills over from an upper part of the second region.

In the second region that is different from the first region, into which the treatment liquid flows from the second path, and stores the treatment liquid overflowed from the first region, the pressure measurement of the treatment liquid by the pressure measurement part is carried out. Herein, since there is no variation caused by the flow of the treatment liquid, which flows in from the second path, reflected by the bottom part of the measurement tank, the liquid surface of the treatment liquid in the second region has smaller variations compared with the liquid surface of the treatment liquid in the first region. Therefore, the pressure of the treatment liquid can be measured by the pressure measurement part with high precision.

Preferably, the first path returns, to the lower part of the first tank, the treatment liquid flowed into a second tank into which the treatment liquid spilled over from the upper part of the first tank flows, the measurement tank is disposed in the second tank, and the treatment liquid spilled over from the upper part of the measurement tank flows into the second tank.

Since the measurement tank is disposed in the second tank, the treatment liquid spilled over from the upper part of the measurement tank flows into the second tank and further flows into the first path. Therefore, the treatment liquid caused to flow into the second path for pressure measurement can be returned to the first path again, and the treatment liquid can be effectively utilized for treating the substrates. Moreover, since the measurement tank is disposed in the second tank, piping or the like for returning the treatment liquid, which has flowed into the second path, to the first path is not required to be separately prepared.

Preferably, the substrate treatment method further includes the step of supplying an air bubble into the first tank.

The particles in the first tank can be removed.

Preferably, the substrate treatment method further includes the step of heating the treatment liquid returning from the first path to the first tank using a first heating part disposed at the first path.

The temperature of the treatment liquid that returns from the first path to the first tank can be caused to be close to the temperature of the treatment liquid in the first tank. Therefore, temperature changes of the treatment liquid in the measurement tank can be suppressed.

Preferably, the substrate treatment method further includes the step of heating the treatment liquid in the second path using a second heating part disposed at the second path.

The temperature of the treatment liquid that flows into the measurement tank can be caused to be close to the temperature of the treatment liquid in the first tank.

Preferably, at least one hole is formed at a bottom part of the measurement tank.

When the measurement tank is to be taken out from the second tank, the treatment liquid can be prevented from remaining in the measurement tank.

Therefore, it is an object of the present invention to provide the techniques for highly precisely measuring the pressure of the treatment liquid used in treatment of substrates.

These and other objects, features, aspects and advantages of the present invention will become more apparent from the following detailed description of the present invention when taken in conjunction with the accompanying drawings.

DESCRIPTION OF THE PREFERRED EMBODIMENT

Hereinafter, a preferred embodiment will be described with reference to attached drawings.

Note that drawings are schematically shown, constitutions thereof are omitted or simplified appropriately in order to facilitate explanations. The interrelations of the sizes and positions of the constitutions, etc. shown in different drawings are not always precisely described, but are appropriately changeable.

In the description shown below, similar constituent elements are shown with the same reference signs, and the names and functions thereof are also considered to be similar. Therefore, detailed descriptions about them may be omitted in order to avoid redundancy.

In the descriptions described below, even if the terms such as "upper", "lower", "left", "right", "side", "bottom", "front", or "rear" which mean particular positions and directions are used, these terms are used for the sake of convenience in order to facilitate understanding the contents of the preferred embodiment, and these are not related to the directions of actually implemented cases.

In the descriptions described below, even if ordinal numbers such as "first" or "second" are used, these terms are used for the sake of convenience in order to facilitate understanding of the contents of the preferred embodiment, and the present invention is not limited to the order, etc. which can be caused by these ordinal numbers.

Preferred Embodiment

Hereinafter, a substrate treatment apparatus according to the present preferred embodiment will be described.

<About Constitutions of Substrate Treatment Apparatus>

Figure 1:
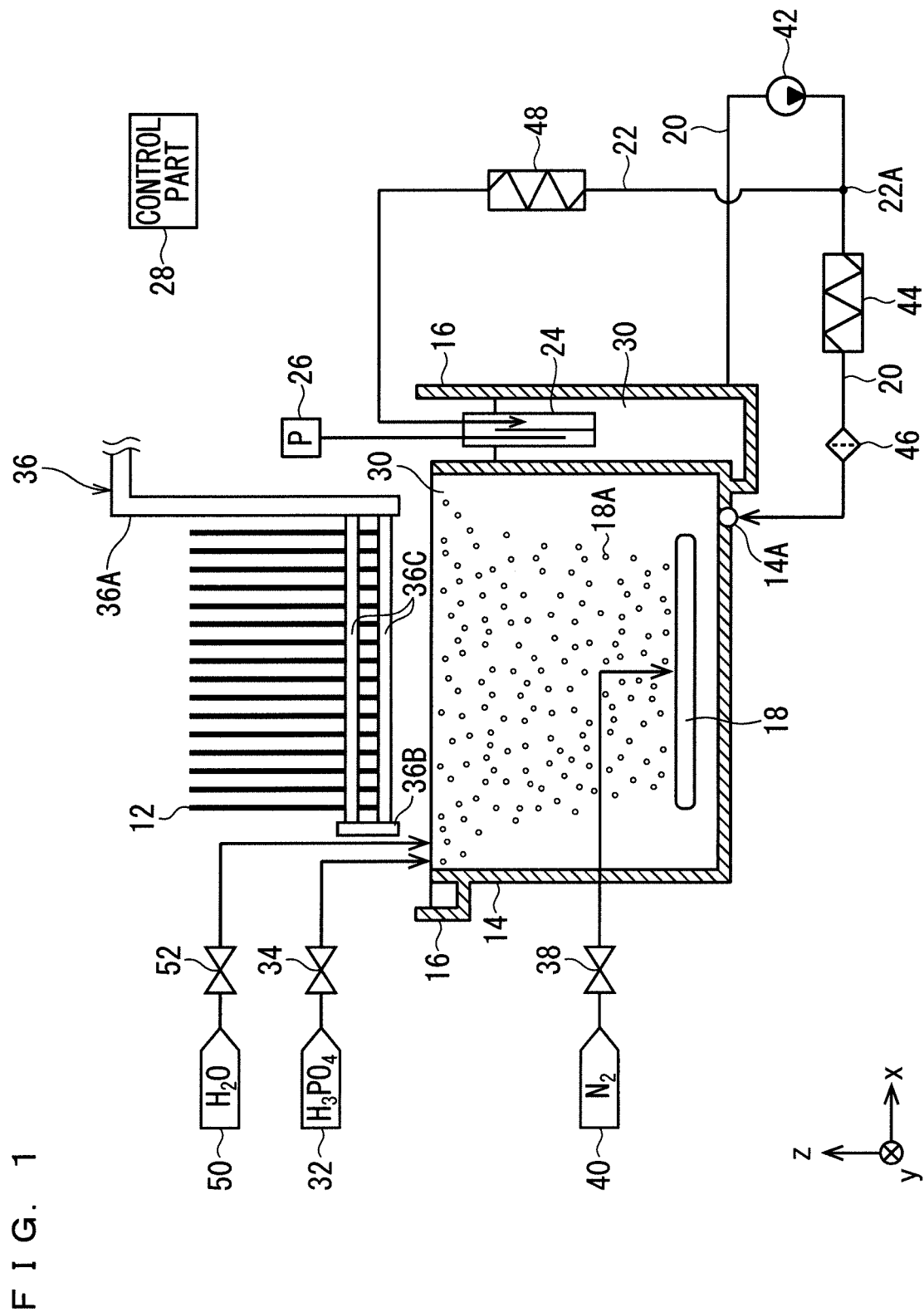
FIG. 1 is a diagram schematically exemplifying the constitutions of a substrate treatment apparatus according to a preferred embodiment.

FIG. 1 is a diagram schematically exemplifying the constitutions of the substrate treatment apparatus according to the present preferred embodiment. In FIG. 1, a substrate 12 is disposed perpendicularly to the surface of the paper, and a plurality of substrates 12, which are similarly disposed, are juxtaposed in an x-axis direction of FIG. 1.

As exemplified in FIG. 1, the substrate treatment apparatus is provided with a treatment tank 14, an outer tank 16, an air-bubble supply part 18, a circulation path 20, a branch path 22, a measurement tank 24, a pressure measurement part 26, and a control part 28.

The substrates 12 are substrates such as semiconductor substrates, liquid-crystal-display glass substrates, or photomask glass substrates. The substrates 12 are retained by a lifter 36. The lifter 36 is provided with a lifter head 36A, a retention plate 36B, and retention rods 36C disposed between the lifter head 36A and the retention plate 36B. A plurality of retention grooves (not illustrated herein) are formed on the retention rods 36C, and the plurality of substrates 12 are retained in an upright orientation in the retention grooves.

The lifter 36 is connected to a lifter drive part (not illustrated herein) having a servomotor, a timing belt, or the like. When the lifter drive part is operated, the lifter 36 moves up/down, in other words, moves in a z-axis direction of FIG. 1. As a result, the substrates 12 can be moved between a treatment position in the treatment tank 14 and a pull-up position above the treatment tank 14. When the substrates 12 are to be treated in the treatment tank 14, the substrates 12 are positioned at the treatment position in the treatment tank 14 by lowering the lifter 36. In the time between the treatment of certain substrates and the treatment of next substrates, the substrates 12 are positioned at the pull-up position above the treatment tank 14 by elevating the lifter 36.

The treatment tank 14 is a container which stores treatment liquid 30 for treating the substrates 12. Cleaning treatment, etc. of the substrates 12 are carried out by immersing the substrates 12 in the treatment liquid 30 stored in the treatment tank 14. The treatment liquid 30 is, for example, pure water or phosphoric acid, which is an etching liquid. The pure water is supplied from a pure-water supply source 50 by opening/closing a valve 52. The phosphoric acid is supplied from a phosphoric-acid supply source 32 by opening/closing a valve 34.

A treatment-liquid discharge opening 14A is provided at a bottom part of the treatment tank 14. The treatment-liquid discharge opening 14A discharges the treatment liquid 30, which flows in the circulation path 20, into the treatment tank 14.

The outer tank 16 is provided to surround the treatment tank 14. As exemplified in FIG. 1, the outer tank 16 has a side provided in an upper part of the treatment tank 14 and a side provided in a range including the upper part to a lower part of the treatment tank 14.

The treatment liquid 30 supplied to the treatment tank 14 spills over, in other words, overflows from the upper part of the treatment tank 14. Then, the treatment liquid 30 flows into the outer tank 16 surrounding the treatment tank 14.

The air-bubble supply part 18 is a device which generates air bubbles 18A such as microbubbles, which are minute air bubbles having a diameter of 50 μm or less, for removing the particles in the treatment tank 14. The air bubbles of the air-bubble supply part 18 are supplied from a gas supply source 40 by opening/closing a valve 38. Note that the air-bubble supply part 18 is not required to be provided.

The circulation path 20 is a path which returns the treatment liquid 30, which has overflowed from the upper part of the treatment tank 14 and further flowed into the outer tank 16, again to the treatment-liquid discharge opening 14A at a lower part of the treatment tank 14. The circulation path 20 is a path which has one end connected to, for example, a bottom part of the outer tank 16, has another end connected to the treatment-liquid discharge opening 14A of the treatment tank 14, and is formed by piping for flowing the treatment liquid 30.

As exemplified in FIG. 1, a pump 42 for flowing the treatment liquid 30, a heater 44 for heating the treatment liquid 30 which returns to the treatment tank 14 from the circulation path 20, and a filter 46 for removing the particles in the treatment liquid 30 flowing in the circulation path 20 are disposed on the circulation path 20. Note that the disposed positions of the pump 42, the heater 44, and the filter 46 on the circulation path 20 are not limited to those of the case exemplified in FIG. 1.

The branch path 22 is a path which branches at a branch point 22A from the circulation path 20 and flows the treatment liquid 30 to the measurement tank 24 of the outer tank 16. The branch path 22 is a path which has one end connected to the branch point 22A of the circulation path 20, has another end guided into the measurement tank 24, and is formed by piping for flowing the treatment liquid 30. The flow rate of the treatment liquid 30 in the branch path 22 is desired to be smaller than the flow rate of the treatment liquid 30 which returns to the treatment tank 14 through the circulation path 20. For example, in a case in which the flow rate of the treatment liquid 30 in the circulation path 20 is 30 L, the flow rate of the treatment liquid 30 in the branch path 22 is desired to be 1 L.

Note that the position of the branch point 22A is not limited to the location exemplified in FIG. 1. In other words, the position of the branch point 22A is not limited to be in the downstream of the pump 42 and in the upstream of the heater 44 on the circulation path 20.

As exemplified in FIG. 1, a heater 48 for heating the treatment liquid 30 in the branch path 22 may be disposed on the branch path 22.

The measurement tank 24 stores the treatment liquid 30 which has flowed in from the branch path 22. The measurement tank 24 is disposed in the outer tank 16. An upper end of the measurement tank 24 is positioned above the liquid surface of the treatment liquid 30 of the outer tank 16, in other words, positioned in the positive direction of the z-axis direction of FIG. 1. The measurement tank 24 causes the treatment liquid 30 to overflow from the upper part of the measurement tank 24 so that the treatment liquid flows into the outer tank 16. In the case exemplified in FIG. 1, the measurement tank 24 is disposed in the outer tank 16. However, the disposed position of the measurement tank 24 is not limited to this location. In other words, the disposed position of the measurement tank 24 is only required to be at the location into which the treatment liquid 30 flows from the branch path 22.

The pressure measurement part 26 is disposed in the measurement tank 24 and measures the pressure of the treatment liquid 30, which is stored in the measurement tank 24, at a predetermined depth. Details will be described later.

The control part 28 is electrically connected to the lifter drive part, the valve 34, the valve 52, the valve 38, the pump 42, the heater 44, the heater 48, etc. so as to control operations thereof. The control part 28 receives the measurement results of the pressure measurement part 26.

The control part 28 is, for example, a central processing unit (CPU), a microprocessor, a microcomputer, or a digital signal processor (DSP) which executes a program(s) stored in an internal or external storage medium. Note that the function of the control part 28 may be realized, for example, by cooperation of a plurality of processing circuits.

<About Constitution of Measurement Tank>

Figure 2:
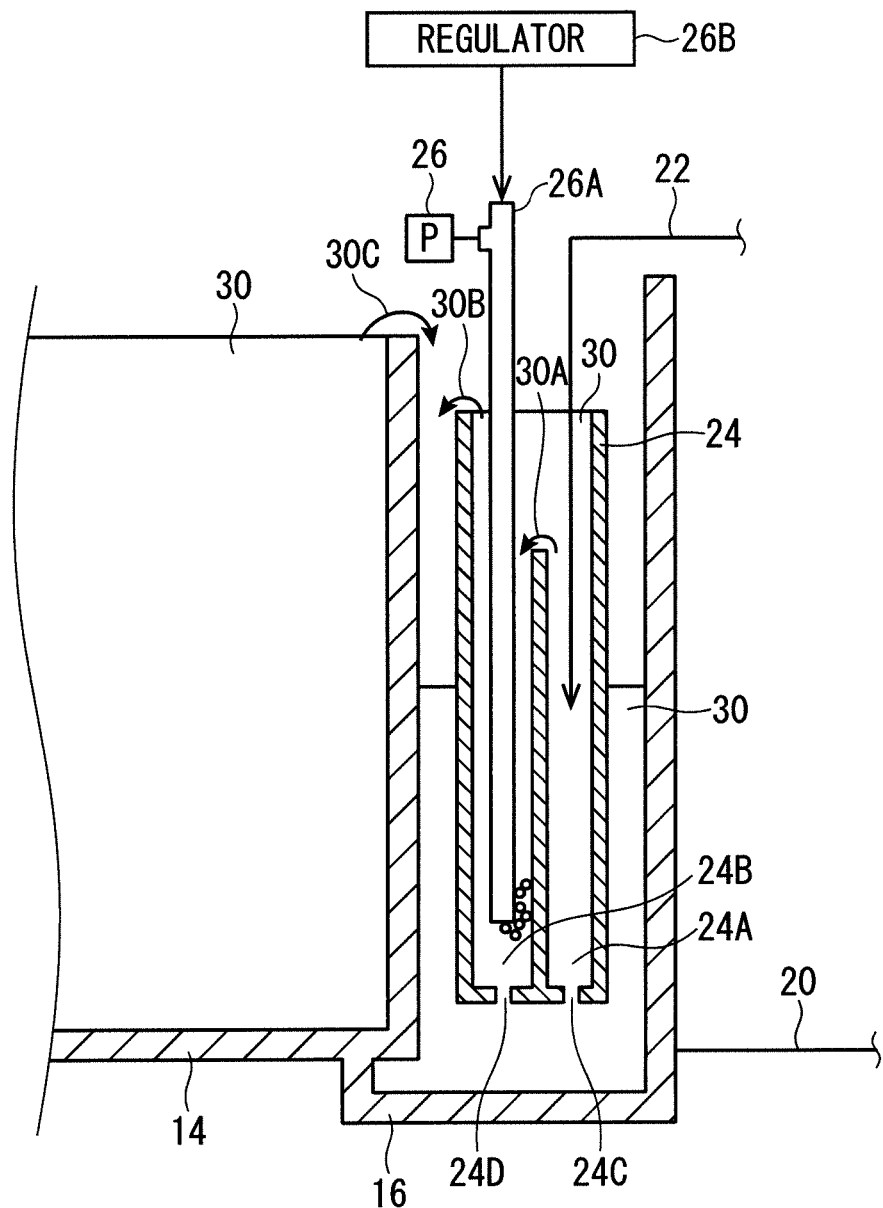
FIG. 2 is a diagram exemplifying a measurement tank according to the preferred embodiment and the constitutions thereof around.

FIG. 2 is a diagram exemplifying the measurement tank according to the present preferred embodiment and the constitutions therearound.

As exemplified in FIG. 2, the measurement tank 24 is provided with a region 24A, which stores the treatment liquid 30 flowed thereinto from the branch path 22, and a region 24B, which stores the treatment liquid 30 spilled over from the upper part of the region 24A. The pressure measurement part 26 measures the pressure of the treatment liquid 30, which is stored in the region 24B, at a predetermined depth of the region 24B.

The treatment liquid 30, which flows from the branch path 22 into the measurement tank 24, is stored in the region 24A first. Then, as exemplified by an arrow 30A, the treatment liquid 30 stored in the region 24A overflows from the upper part of the region 24A.

Furthermore, the treatment liquid 30, which has overflowed from the upper part of the region 24A, is stored in the region 24B. Then, as exemplified by an arrow 30B, the treatment liquid 30 stored in the region 24B overflows from the upper part of the region 24B and flows into the outer tank 16. Note that, as exemplified by an arrow 30C, the liquid 30 flows into the outer tank 16 also from the treatment tank 14.

A hole 24C and a hole 24D may be formed at a bottom part of the measurement tank 24. Since the holes are formed at the bottom part of the measurement tank 24, when the measurement tank 24 is to be taken out from the outer tank 16, the treatment liquid 30 can be prevented from remaining in the measurement tank 24. However, in the case in which the hole 24C and the hole 24D are formed, the treatment liquid 30 in the measurement tank 24 flows out to the outer tank 16 from these holes; therefore, the flow rate of the treatment liquid 30 which flows into the measurement tank 24 from the branch path 22 has to be adjusted so that the treatment liquid 30 continuously overflows from the upper part of the measurement tank 24. This adjustment operation is carried out, for example, by the control part 28. Note that the holes at the bottom part of the measurement tank 24 are not required to be formed. Even in the case in which the holes are formed, the holes are not limited to the shapes and the number exemplified in FIG. 2.

The pressure measurement part 26 measures the pressure of the treatment liquid 30, which is stored in the region 24B, at a predetermined depth. Herein, for example, if the treatment liquid is a phosphoric acid solution, there is a correlation between the concentration of phosphoric acid and the specific weight of the phosphoric acid. Furthermore, there is a correlation between the specific weight of the phosphoric acid and the pressure of the phosphoric acid at the predetermined depth. Therefore, based on these correlations, by measuring the pressure of the treatment liquid 30, which is stored in the region 24B, at the predetermined depth from the liquid surface thereof by the pressure measurement part 26, for example, the concentration of the phosphoric acid solution can be measured.

The pressure measurement part 26 is connected to a supply tube 26A. The supply tube 26A is immersed in the treatment liquid 30 stored in the region 24B, and a lower end of the supply tube 26A reaches the predetermined depth from the liquid surface of the treatment liquid 30 in the region 24B. A certain amount of gas such as nitrogen gas is supplied to the supply tube 26A by a regulator 26B.

In a steady state, the release pressure of the nitrogen gas released from the lower end of the supply tube 26A can be considered to be approximately equal to the pressure at the predetermined depth from the liquid surface of the treatment liquid 30 in the region 24B. The pressure measurement part 26 measures the pressure of the above described nitrogen gas in the supply tube 26A. Then, the pressure measurement part 26 outputs a voltage value equal to or higher than 0 V and equal to or lower than 2.5 V in accordance with the measured pressure of the nitrogen gas.

In a case in which the concentration of the treatment liquid 30 is to be measured based on the pressure of the treatment liquid 30 at the predetermined depth from the liquid surface thereof, the concentration of the treatment liquid 30 is calculated while the voltage output from the pressure measurement part 26 is subjected to referencing of data describing the correlation of the pressure and the specific weight and the data describing the correlation between the specific weight and the concentration stored in a storage medium or the like in advance.

<About Operation of Substrate Treatment Apparatus>

Figure 3:
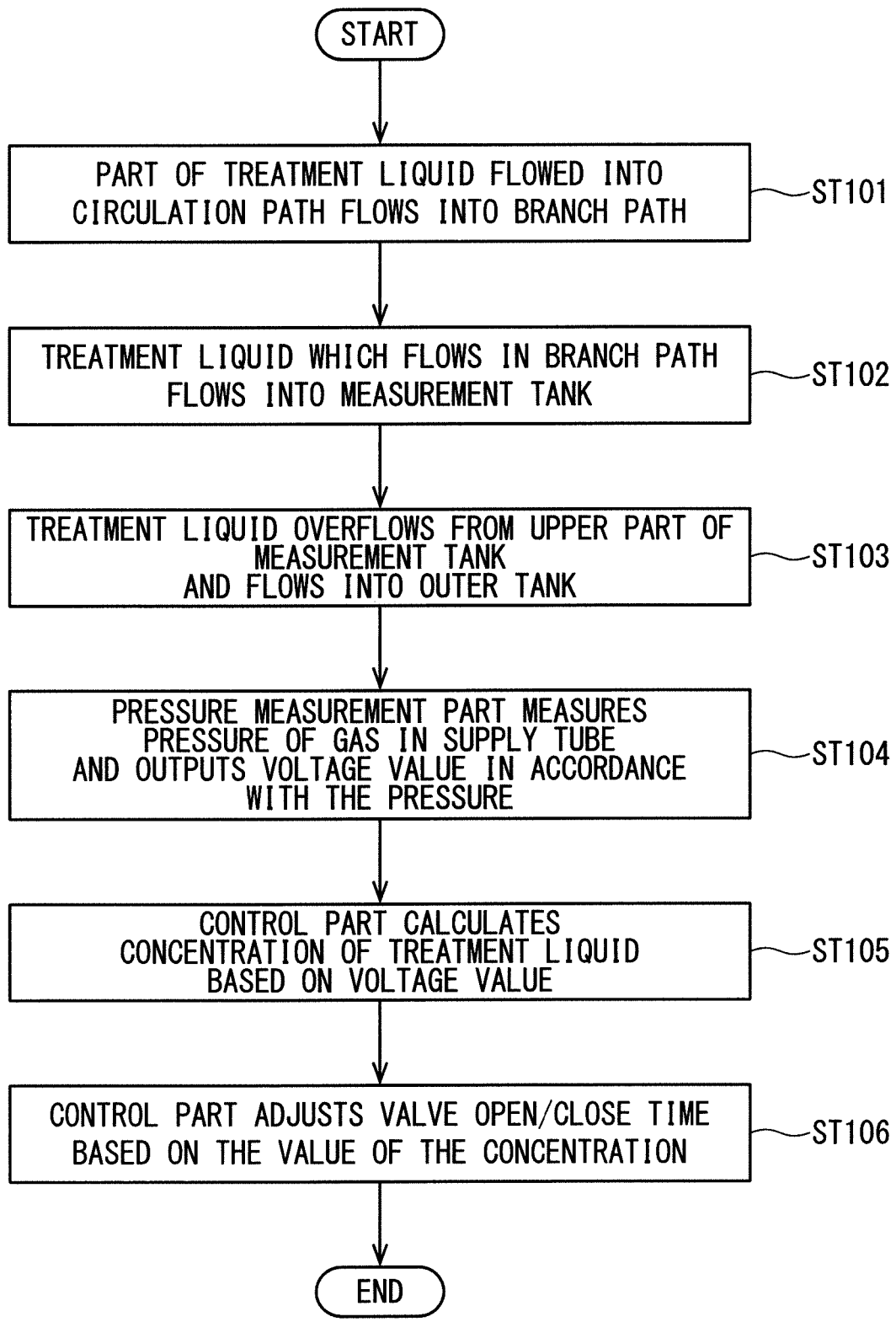
FIG. 3 is a flow chart exemplifying the operation of the substrate treatment apparatus according to the preferred embodiment.

Next, operation of the substrate treatment apparatus according to the present preferred embodiment will be described with reference to FIG. 1 to FIG. 3. Particularly, a case in which the concentration control of the treatment liquid 30 in the treatment tank 14 is carried out by the control part 28 in accordance with the measurement result from the pressure measurement part 26 of the measurement tank 24 will be described. Herein, FIG. 3 is a flow chart exemplifying the operation of the substrate treatment apparatus according to the present preferred embodiment.

First, as exemplified in FIG. 1, when the lifter 36 is lowered, the substrates 12 are positioned at the treatment position in the treatment tank 14. Then, cleaning treatment, etc. of the substrates 12 are carried out by immersing the substrates 12 in the treatment liquid 30 stored in the treatment tank 14. In order to remove the particles in the treatment tank 14, the air bubbles 18A are supplied into the treatment tank 14 by the air-bubble supply part 18. On the other hand, as a result of supplying of pure water and phosphoric acid to the treatment tank 14, the treatment liquid 30 overflows from the treatment tank 14. Then, the treatment liquid 30 overflowed from the treatment tank 14 flows into the outer tank 16.

Then, the treatment liquid 30 stored in the outer tank 16 flows into the circulation path 20. Then, part of the treatment liquid 30 flowed into the circulation path 20 flows into the branch path 22 from the branch point 22A (step ST101 exemplified in FIG. 3).

The treatment liquid 30 which flows in the circulation path 20 in the downstream of the branch point 22A is subjected to temperature adjustment by the heater 44 and removal of the particles in the treatment liquid 30 by the filter 46. Herein, the temperature control of the heater 44 is carried out by the control part 28.

The temperature of the treatment liquid 30 which flows in the circulation path 20 in the downstream of the branch point 22A becomes close to the temperature of the treatment liquid 30 in the treatment tank 14 as a result of carrying out the temperature adjustment by the heater 44. Moreover, since the particles in the treatment liquid 30 which flows in the circulation path 20 in the downstream of the branch point 22A are removed by the filter 46, the particles can be prevented from being mixed into the treatment tank 14.

Then, the treatment liquid 30 which flows in the circulation path 20 in the downstream of the branch point 22A is discharged into the treatment tank 14 from the treatment-liquid discharge opening 14A.

On the other hand, the treatment liquid 30 which flows in the branch path 22 in the downstream of the branch point 22A is subjected to temperature adjustment by the heater 48 and then flows into the measurement tank 24 (step ST102 exemplified in FIG. 3). Herein, the temperature control of the heater 48 is carried out by the control part 28.

The treatment liquid 30 which flows in the branch path 22 in the downstream of the branch point 22A is subjected to temperature adjustment by the heater 48, and, as a result, the temperature of the treatment liquid 30 that flows into the measurement tank 24 can be caused to be close to the temperature of the treatment liquid 30 in the treatment tank 14. By virtue of this, pressure measurement, specific weight measurement, and concentration measurement can be carried out for the treatment liquid 30 in the measurement tank 24 under the equivalent conditions as those of the treatment liquid 30 in the treatment tank 14.

In the measurement tank 24, as exemplified in FIG. 2, first, the treatment liquid 30 flows into the region 24A. Then, the treatment liquid 30 overflows from the upper part of the region 24A and flows into the region 24B. Furthermore, the treatment liquid 30 overflows from the upper part of the region 24B and flows into the outer tank 16 (step ST103 exemplified in FIG. 3). The treatment liquid 30 stored in the outer tank 16 flows into the circulation path 20.

Herein, the lower end of the supply tube 26A connected to the pressure measurement part 26 is positioned at the predetermined depth in the region 24B. Herein, since the regulator 26B supplies a certain amount of gas to the supply tube 26A to achieve a steady state, the release pressure of the nitrogen gas released from the lower end of the supply tube 26A can be considered to be approximately equivalent to the pressure of the treatment liquid 30 in the region 24B at the predetermined depth from the liquid surface thereof. The pressure measurement part 26 measures the pressure of the gas in the supply tube 26A immersed in the treatment liquid 30, which is in a state of a stable liquid surface as a result of the overflow from the upper part of the region 24B, and outputs a voltage value in accordance with the pressure (step ST104 exemplified in FIG. 3).

As exemplified in FIG. 1, the voltage value output from the pressure measurement part 26 is received by the control part 28. The control part 28 calculates the concentration of the treatment liquid 30 based on the voltage value (step ST105 exemplified in FIG. 3). Then, based on the value of the concentration, the control part 28, for example, adjusts the open/close time of the valve 34 and the valve 52 (step ST106 exemplified in FIG. 3). By virtue of this, the control part 28 carries out concentration control of the treatment liquid 30 in the treatment tank 14.

Effects Brought about by the Preferred Embodiment Described Above

Next, the effects brought about by the preferred embodiment described above are exemplified. Note that, in the following description, the effects are described based on the specific constitutions exemplified in the preferred embodiment described above. However, within the range that brings about similar effects, the constitutions may be replaced by other specific constitutions exemplified in the present specification.

According to the preferred embodiment described above, a substrate treatment apparatus is provided with a first tank, a first path, a second path, the measurement tank 24, and the pressure measurement part 26. The first tank stores the treatment liquid 30 for treating the substrates 12. The first path returns the treatment liquid 30, which has spilled over from the upper part of the first tank, to the lower part of the first tank. The second path branches from the first path. The measurement tank 24 stores the treatment liquid 30 which has flowed in from the second path. In a state in which the treatment liquid 30 spills over from the upper part of the measurement tank 24, the pressure measurement part 26 measures the pressure of the treatment liquid 30 at the predetermined depth in the measurement tank 24. Herein, the first tank corresponds to, for example, the treatment tank 14. The first path corresponds to, for example, the circulation path 20. The second path corresponds to, for example, the branch path 22.

According to such constitutions, in the measurement tank 24, variations in the liquid surface of the treatment liquid 30 can be suppressed by overflowing the treatment liquid 30, which flows in from the branch path 22, from the upper part. Therefore, the pressure of the treatment liquid 30 which is in the stable state of liquid surface in the measurement tank 24 is measured by the pressure measurement part 26, and, as a result, the pressure of the treatment liquid 30 can be measured with high precision.

Note that the other constitutions exemplified in the specification of the present application other than these constitutions can be appropriately omitted. In other words, with at least these constitutions, the effects described above can be brought about.

However, even if at least one of the other constitutions exemplified in the specification of the present application is appropriately added to the constitutions described above, in other words, even if another constitution(s) exemplified in the specification of the present application not described as the constitutions described above is added to the constitutions described above, effects similar to those described above can be brought about.

According to the preferred embodiment described above, the flow rate of the treatment liquid 30 in the branch path 22 is smaller than the flow rate of the treatment liquid 30 which returns to the treatment tank 14 through the circulation path 20. According to such constitutions, by carrying out pressure measurement by using the treatment liquid 30 in the branch path 22 having the smaller flow rate than that of the treatment liquid 30 in the circulation path 20, the precision of the pressure measurement of the treatment liquid 30 by the pressure measurement part 26 can be increased. More specifically, in the measurement tank 24, variations in the liquid surface of the treatment liquid 30 are suppressed by overflowing the treatment liquid 30, which flows in from the branch path 22, from the upper part, in which, if the flow rate of the treatment liquid 30 which flows in from the branch path 22 is low, the flow rate of the treatment liquid 30 which overflows from the upper part of the measurement tank 24 is also lowered, and therefore, the variations in the liquid surface are reduced. Therefore, the precision of the pressure measurement of the treatment liquid 30 by the pressure measurement part 26 can be increased.

According to the preferred embodiment described above, the measurement tank 24 is provided with a first region and a second region. The treatment liquid 30 flows into the first region from the branch path 22. The treatment liquid 30 spilled over from the first region flows into the second region. Then, the pressure measurement part 26 measures the pressure of the treatment liquid 30 in the second region in the state in which the treatment liquid 30 spills over from the upper part of the second region. Herein, the first region corresponds to, for example, the region 24A. The second region corresponds to, for example, the region 24B. According to such constitutions, in the region 24B that is different from the region 24A, into which the treatment liquid 30 flows from the branch path 22, and that stores the treatment liquid 30 overflowed from the region 24A, pressure measurement of the treatment liquid 30 by the pressure measurement part 26 is carried out. Herein, since there is no variation caused by the flow of the treatment liquid 30, which flows in from the branch path 22, reflected by the bottom part of the measurement tank 24, the liquid surface of the treatment liquid 30 in the region 24B has smaller variations compared with the liquid surface of the treatment liquid 30 in the region 24A. Therefore, the pressure of the treatment liquid 30 can be measured by the pressure measurement part 26 with high precision.

According to the preferred embodiment described above, the substrate treatment apparatus is provided with a second tank into which the treatment liquid 30 spilled over from the upper part of the treatment tank 14 flows. The circulation path 20 returns the treatment liquid 30, which has flowed into the second tank, to the lower part of the treatment tank 14. The measurement tank 24 is disposed in the second tank. Then, the treatment liquid 30 spilled over from the upper part of the measurement tank 24 flows into the second tank. Herein, the second tank corresponds to, for example, the outer tank 16. According to such constitutions, since the measurement tank 24 is disposed in the outer tank 16, the treatment liquid 30 spilled over from the upper part of the measurement tank 24 flows into the outer tank 16 and further flows into the circulation path 20. Therefore, the treatment liquid 30 caused to flow into the branch path 22 for pressure measurement can be returned to the circulation path 20 again, and the treatment liquid 30 can be effectively utilized for treating the substrates 12. Moreover, since the measurement tank 24 is disposed in the outer tank 16, piping or the like for returning the treatment liquid 30, which has flowed into the branch path 22, to the circulation path 20 is not required to be separately prepared. Moreover, if the measurement tank 24 is disposed at a location having a sufficient depth in the outer tank 16, a depth-direction length necessary for increasing the precision of pressure measurement can be sufficiently ensured. In other words, the pressure measurement can be carried out while the lower end of the supply tube 26A is dipped to the depth sufficiently distant from the liquid surface of the treatment liquid 30. Note that, since the upper end of the measurement tank 24 is positioned above the liquid surface of the treatment liquid 30 in the outer tank 16, the influence of the variations in the liquid surface of the treatment liquid 30 in the outer tank 16 with respect to the liquid surface of the treatment liquid 30 in the measurement tank 24 can be prevented.

Moreover, according to the preferred embodiment described above, the substrate treatment apparatus is provided with the air-bubble supply part 18, which supplies air bubbles in the treatment tank 14. According to such constitutions, the particles in the treatment tank 14 can be removed. Note that, if the air bubbles 18A are supplied in the treatment tank 14 by the air-bubble supply part 18, the variations in the liquid surface of the treatment liquid 30 in the treatment tank 14 become more notable. In such a case, for example, if the pressure of the treatment liquid 30 in the treatment tank 14 is measured, the measurement precision is lowered due to the influence of the variations in the liquid surface of the treatment liquid 30. On the other hand, if the pressure of the treatment liquid 30 in the measurement tank 24 is measured by the pressure measurement part 26 like the case of the above described preferred embodiment, the pressure of the treatment liquid 30 can be measured with high precision even when the liquid surface of the treatment liquid 30 in the treatment tank 14, furthermore, the liquid surface of the treatment liquid 30 in the outer tank 16 largely vary.

Moreover, according to the preferred embodiment described above, the substrate treatment apparatus is provided with a first heating part which is disposed at the circulation path 20 and heats the treatment liquid 30, which returns to the treatment tank 14 from the circulation path 20.

Herein, the first heating part corresponds to, for example, the heater 44. According to such constitutions, the temperature of the treatment liquid 30 which flows in the circulation path 20 can be caused to be close to the temperature of the treatment liquid 30 in the treatment tank 14. Therefore, temperature changes of the treatment liquid 30 in the measurement tank 24 can be suppressed.

Moreover, according to the preferred embodiment described above, the substrate treatment apparatus is provided with a second heating part which is disposed at the branch path 22 and heats the treatment liquid 30 in the branch path 22. Herein, the second heating part corresponds to, for example, the heater 48. According to such constitutions, the temperature of the treatment liquid 30 which flows into the measurement tank 24 can be caused to be close to the temperature of the treatment liquid 30 in the treatment tank 14. Therefore, pressure measurement, specific weight measurement, and concentration measurement can be carried out for the treatment liquid 30 in the measurement tank 24 under the equivalent conditions as those of the treatment liquid 30 in the treatment tank 14.

Moreover, according to the preferred embodiment described above, the hole 24C and the hole 24D are formed in the bottom part of the measurement tank 24. According to such constitutions, when the measurement tank 24 is to be taken out from the outer tank 16, the treatment liquid 30 can be prevented from remaining in the measurement tank 24.

About Modified Examples of Preferred Embodiment Described Above

In the preferred embodiment described above, the quality of materials, materials, dimensions, shapes, relative disposition relations, conditions of implementation, etc. of the constituent elements are described in some cases. However, these are examples in all aspects, and they are not limited to those described in the specification of the present application.

Therefore, numerous modified examples and equivalents which are not shown as examples assumed to be in the scope of the techniques disclosed in the specification of the present application. For example, a case in which at least one constituent element is modified, a case in which it is added, and a case in which it is omitted are included.

While the invention has been shown and described in detail, the foregoing description is in all aspects illustrative and not restrictive. It is therefore understood that numerous modifications and variations can be devised without departing from the scope of the invention.

What is claimed is:

1. A substrate treatment apparatus comprising:
    a first tank that stores treatment liquid for treating a substrate;
    a first path that returns said treatment liquid spilled over from an upper part of said first tank to a lower part of said first tank;
    a second path that branches from said first path;
    a measurement tank that is provided with a first region into which said treatment liquid flows from said second path and a second region into which said treatment liquid spilled over from an upper part of said first region flows and stores said treatment liquid flowed in from said second path; and
    a pressure sensor that measures a pressure of said treatment liquid at a predetermined depth in said measurement tank in a state in which said treatment liquid is spilling over from an upper part of said second region.

2. The substrate treatment apparatus according to claim 1, wherein
    a flow rate of said treatment liquid in said second path is smaller than a flow rate of said treatment liquid that returns to said first tank through said first path.

3. The substrate treatment apparatus according to claim 1, further comprising
    a second tank into which said treatment liquid spilled over from the upper part of said first tank flows, wherein
    said first path returns said treatment liquid flowed into said second tank to the lower part of said first tank,
    said measurement tank is disposed in said second tank, and
    said treatment liquid spilled over from the upper part of said measurement tank flows into said second tank.

4. The substrate treatment apparatus according to claim 1, further comprising
    an air-bubble generator that supplies air bubbles into said first tank.

5. The substrate treatment apparatus according to claim 1, further comprising
    a first heater that is disposed at said first path and heats said treatment liquid returning from said first path to said first tank.

6. The substrate treatment apparatus according to claim 1, further comprising
    a second heater that is disposed at said second path and heats said treatment liquid in said second path.

7. The substrate treatment apparatus according to claim 1, wherein
    at least one hole is formed at a bottom part of said measurement tank.

8. A substrate treatment apparatus comprising:
    a first tank that stores treatment liquid for treating a substrate;
    a second tank into which said treatment liquid spilled over from an upper part of said first tank flows;
    a first path that returns said treatment liquid spilled over from the upper part of said first tank and flowing into said second tank to a lower part of said first tank;
    a second path that branches from said first path;
    a measurement tank that is disposed in said second tank and stores said treatment liquid flowed in from said second path; and
    a pressure sensor that measures a pressure of said treatment liquid at a predetermined depth in said measurement tank in a state when said treatment liquid is spilling over from an upper part of said measurement tank and flows into said second tank.

9. The substrate treatment apparatus according to claim 8, wherein
    said measurement tank is provided with a first region into which said treatment liquid flows from said second path and a second region into which said treatment liquid spilled over from an upper part of said first region flows, and
    said pressure sensor measures the pressure of said treatment liquid in said second region in a state in which said treatment liquid is spilling over from an upper part of said second region.

10. The substrate treatment apparatus according to claim 8, wherein
    a flow rate of said treatment liquid in said second path is smaller than a flow rate of said treatment liquid that returns to said first tank through said first path.

11. The substrate treatment apparatus according to claim 8, wherein at least one hole is formed at a bottom part of said measurement tank.

\* \* \* \* \*